United States Patent [19]

Kato et al.

[11] Patent Number: 5,566,244

[45] Date of Patent: Oct. 15, 1996

[54] METHOD OF INSPECTING A WORKPIECE SURFACE INCLUDING A PICTURING SYSTEM WITH A SHORTENED FOCAL PLANE

[75] Inventors: Norihide Kato; Kenichiro Mori; Tomohide Shimizu, all of Sayama, Japan

[73] Assignee: Honda Giken Kogyo Kabushiki Kaisha, Tokyo, Japan

[21] Appl. No.: 341,083

[22] Filed: Nov. 17, 1994

[30] Foreign Application Priority Data

Nov. 22, 1993 [JP] Japan ................... 5-292109
Dec. 2, 1993 [JP] Japan ................... 5-302940
Dec. 8, 1993 [JP] Japan ................... 5-307788

[51] Int. Cl.$^6$ .......................................... G06K 9/00
[52] U.S. Cl. ........................... 382/108; 382/152; 348/128
[58] Field of Search .................... 382/108, 141, 382/270, 321, 152; 348/128, 131; 356/123, 237, 369, 371, 376, 445

[56] References Cited

U.S. PATENT DOCUMENTS

| | | | |
|---|---|---|---|
| 4,863,268 | 9/1989 | Clarke et al. | 356/237 |
| 4,868,404 | 9/1989 | Hajime | 250/572 |
| 4,920,572 | 4/1990 | Sugita et al. | 382/48 |
| 4,958,223 | 9/1990 | Juvinall et al. | 358/106 |
| 4,974,077 | 11/1990 | Kusaba | 358/101 |
| 4,975,972 | 12/1990 | Bose et al. | 382/8 |
| 4,980,923 | 12/1990 | Kawamoto et al. | 382/41 |
| 5,047,858 | 9/1991 | Aimonoya | 358/183 |
| 5,155,558 | 10/1992 | Tannenbaum et al. | 356/446 |
| 5,237,404 | 8/1993 | Tanaka et al. | 358/106 |

FOREIGN PATENT DOCUMENTS

| | | | |
|---|---|---|---|
| 0094824 | 11/1983 | European Pat. Off. | G06F 15/20 |
| 0198481 | 10/1986 | European Pat. Off. | G06F 15/70 |
| 0209252 | 1/1987 | European Pat. Off. | G06K 9/00 |
| 0263473 | 4/1988 | European Pat. Off. | G01N 21/88 |
| 0374977 | 12/1989 | European Pat. Off. | G01B 11/30 |
| 0371650 | 6/1990 | European Pat. Off. | G01B 11/06 |
| 5-14902 | 2/1993 | Japan | G01N 21/88 |
| 5-164703 | 6/1993 | Japan | G01N 21/88 |
| 1549706 | 8/1979 | United Kingdom | G01N 21/00 |
| 2032618 | 5/1980 | United Kingdom | G01B 11/00 |
| 2102119 | 1/1983 | United Kingdom | G01B 11/02 |
| 2115141 | 1/1983 | United Kingdom | G01N 21/55 |
| 2104651 | 3/1983 | United Kingdom | G01N 21/90 |
| 2184538 | 6/1987 | United Kingdom | H05K 13/08 |
| 2221032 | 1/1990 | United Kingdom | G01N 21/89 |
| 2239089 | 6/1991 | United Kingdom | G01N 21/88 |
| 2262339 | 6/1993 | United Kingdom | G01N 21/88 |
| WO85/03776 | 1/1985 | WIPO | G01N 21/88 |
| WO91/16619 | 10/1991 | WIPO | G01N 21/88 |

Primary Examiner—Leo Boudreau
Assistant Examiner—Andrew W. Johns
Attorney, Agent, or Firm—Armstrong, Westerman, Hattori, McLeland & Naughton

[57] ABSTRACT

A workpiece surface is measured to detect a defective portion with a projection and a depression on the workpiece surface by using an optical inspecting apparatus having a projector for radiating a detecting light towards the workpiece surface and a picturing device for receiving a reflected light from the workpiece surface. A reflected light from the workpiece surface is pictured in a condition in which a focal surface of the picturing device is positioned away from the workpiece surface to the side of the picturing device relative to an entire region of that effective inspecting range of the workpiece surface from which the picturing device can receive the reflected light. The defective portion on the workpiece surface is detected from a dark portion which appears on the image of the picturing device.

5 Claims, 6 Drawing Sheets

METHOD OF INSPECTING A WORKPIECE SURFACE INCLUDING A PICTURING SYSTEM WITH A SHORTENED FOCAL PLANE

BACKGROUND OF THE INVENTION

1. Field of the Invention

The present invention relates to a method of inspecting a surface of a workpiece (hereinafter called a workpiece surface) in order to detect a defect or smoothness of the surface such as a painted surface or the like of the workpiece.

2. Description of Related Art

A conventional method of inspecting of this kind is disclosed in Japanese Published Unexamined Utility Model Registration Application No. 14902/1993. Namely, as shown in FIG. 8A, by using an optical inspecting apparatus having a projecting means 1 for radiating an inspecting light towards a workpiece surface A and a picturing means 2 for receiving a reflected light from the workpiece surface A, painting conditions of the workpiece surface A are checked based on the image data of the reflected light to be formed into an image (or image-formed) on the picturing means 2. The adhesion of dust, the presence or absence of scratches, or the like is thus inspected.

In this prior art, the projecting means 1 is made up of a light source 10 and an optical converging system 11 such as a Fresnel lens or the like which radiates the light from the light source 10 towards the workpiece surface A. It is thus so arranged that the radiated light is converged towards the picturing means 2 through the convergence of the detecting light by the optical converging system 11. In this manner, the effective inspection range of the workpiece surface A from which the picturing means 2 can receive the reflected light is enlarged.

The picturing means 2 is made up of a CCD camera which has an image screen 20 on which picture elements made up of CCD elements are arrayed and an optical image-forming system 21 in which a plurality of lenses are combined. The position and the focal length of the picturing means 2 are adjusted such that a focal surface 22 coincides with the workpiece surface A in the central position of the effective inspection range. Inspection is carried out, in this condition, based on the data of an image of reflected light which is formed on the image surface 20 of the picturing means 2.

In this case, if a defective portion B with a projection and a depression exists on the workpiece surface A, the reflected light R from the defective portion B will no longer be received by the picturing means 2, and a dark portion corresponding to the defective portion B will appear on the image of the picturing means 2. Then, a histogram is prepared which represents the number of picture elements for each luminance on the image of the picturing means. The image of the picturing means is binarized on the basis of binarizing a threshold value which is set at a mid-level luminance, between the luminance of the maximum value of the histogram in the bright portion and the luminance of the maximum value of the histogram in the dark portion. The dark portion which is isolated inside the bright portion of the binarized image is determined to be attributable to the defective portion on the workpiece surface. The position and the size of the defective portion are thus detected from the position and the size of the dark portion (see Japanese Published Unexamined Patent Application No. 164703/1993).

However, in the above-described conventional method, a problem exists if the defective portion is small. For example, if a small defective portion B exists on the workpiece surface A, the reflected light R from the defective portion B is received by the picturing means 2, as shown in FIG. 8B. On the image surface 20 thereof the reflected light R is image-formed on the screen in a portion corresponding to the defective portion and, therefore, the defective portion sometimes can not be detected.

In view of the above-described disadvantages, the present invention has an object of providing such a method of inspecting the workpiece surface as will enable to detect even a small defective portion.

SUMMARY OF THE INVENTION

In order to attain the above-described object, the present invention is a method of inspecting a workpiece surface for detecting a defective portion with a projection and a depression on the workpiece surface by using an optical inspecting apparatus having a projector for radiating a detecting light towards the workpiece surface and a picturing means for receiving a reflected light from the workpiece surface. The method comprises the steps of: picturing with the picturing means the reflected light in a condition in which a focal surface of the picturing means is positioned away from the workpiece surface to the side of the picturing means relative to an entire region of that effective inspecting range of the workpiece surface from which the picturing means can receive the reflected light; and processing an image to detect the defective portion on the workpiece surface from a dark portion which appears on the image of the picturing means.

If the focal surface is positioned away from the workpiece surface to the side of the positioning means as described above, even if the reflected light from a small defective portion is received by the picturing means, the reflected light will not be image-formed on the image surface of that portion of the picturing means which corresponds to the defective portion, and therefore the presence of the defective portion can be detected by its appearing as a dark portion.

By the way, there are cases where the luminance distribution of the image in the picturing means becomes uneven because of the irregular radiation or irregular receiving of light due to adhesion of dust or the like on the projecting means or the picturing means, or further because of curved surface portions or the like on the painted surface. As a result, a portion of lower luminance may sometimes appear on the image even if there is no defective portion.

In order to accurately detect the size of the defective portion on the workpiece surface, it is necessary to set the binarizing threshold value at a relatively high luminance so that the portion of relatively high luminance around the dark portion can also be binarized as the dark portion. Then, there is a possibility that a portion which is not defective may also be binarized as the dark portion, due to the unevenness of the luminance distribution, resulting in a faulty detection.

In order to eliminate this kind of disadvantage, the following procedure may be followed, i.e., in the step of processing the image, a predetermined parameter value is obtained for each of picturing elements of the picturing means based on a difference in luminance between one picturing element and its surrounding picturing elements and a dark portion which is positioned in a portion in which the parameter value becomes large is selected as a dark portion which is attributable to the defect on the workpiece surface.

That luminance change in the dark portion which appears, in the image of the picturing means, as a result of unevenness of luminance distribution is relatively gradual. To the contrary, that luminance in the dark portion which is attributable to the defective portion of the workpiece surface varies rapidly.

Therefore, if the parameter value based on the above-described luminance difference is obtained, that parameter value in the dark portion which is attributable to the unevenness of the luminance distribution becomes small and that parameter value in the dark portion which is attributable to the defective portion becomes large.

Even if the image of the picturing means is binarized at a threshold value of a relatively high luminance as described above, among the dark portions appearing on the binarized image, the dark portion which is attributable to the defective portion on the workpiece surface can accurately be selected based on the above-described parameter value. From the position and the area of the selected dark portion, the position and the size of the defective portion on the workpiece surface can accurately be detected.

By the way, in case data of a plurality of items such as the position and the area of each dark portion appearing on the image (including binarized image) of the picturing means are measured, the measurement of the data is conventionally made by sequentially extracting the dark portion by image processing. However, it is necessary in this method to repeat the measuring processes for as many as the number of the dark portions. The processing time of data measurement thus varies with the number of the dark portions. Therefore, in case the inspection is made in an on-line system, it will be necessary to set a cycle time relatively longer taking into consideration a case in which the dark portions appear in a large number, thereby resulting in a poorer efficiency.

In order to eliminate this kind of disadvantage, a labelling image which indicates each of the dark portions, which appear on the image of the picturing means, by different luminances may be prepared and the data of the plurality of items may be measured, based on the labelling image, one by one with respect to all of the dark portions in a lump.

The time of processing required for measuring the data of one item becomes longer than the time required to measure the data of one dark portion when data measuring is made by extracting, one by one, each of the dark portions, but becomes constant regardless of the number of the dark porions. Since the number of items of data to be measured is constant, the total time of processing required for measuring the data of all the items also becomes constant. Accordingly, unlike in the conventional method, at the time of on-line inspection, the cycle time need not be set longer in anticipation for the appearance of a larger number of dark portions. The efficiency of inspection can therefore be improved.

BRIEF DESCRIPTION OF THE DRAWINGS

The above and other objects and the attendant advantages of the present invention will become readily apparent by reference to the following detailed description when considered in conjunction with the accompanying drawings wherein.

DETAILED DESCRIPTION OF A PREFERRED EMBODIMENT

Figure 1:
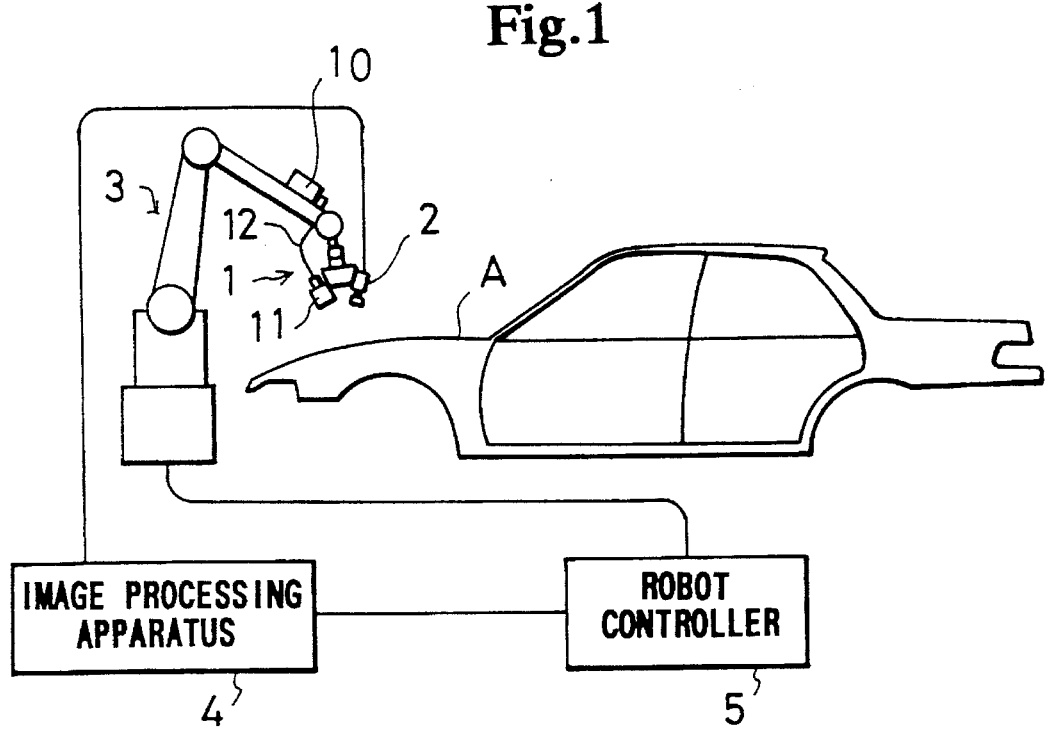
FIG. 1 is a diagram showing a general arrangement of an inspection apparatus to be used for carrying out the present invention.

In the illustrated example, the present invention is applied to the inspection of a painted surface of a workpiece which is made up of a motor vehicle body. As shown in FIG. 1, an optical inspecting apparatus is mounted on an operating end of a robot 3. The inspecting apparatus is sequentially moved by the operation of the robot 3 to each of the inspecting positions as taught in advance, thereby carrying out the inspection of a workpiece surface A.

Figure 8A:
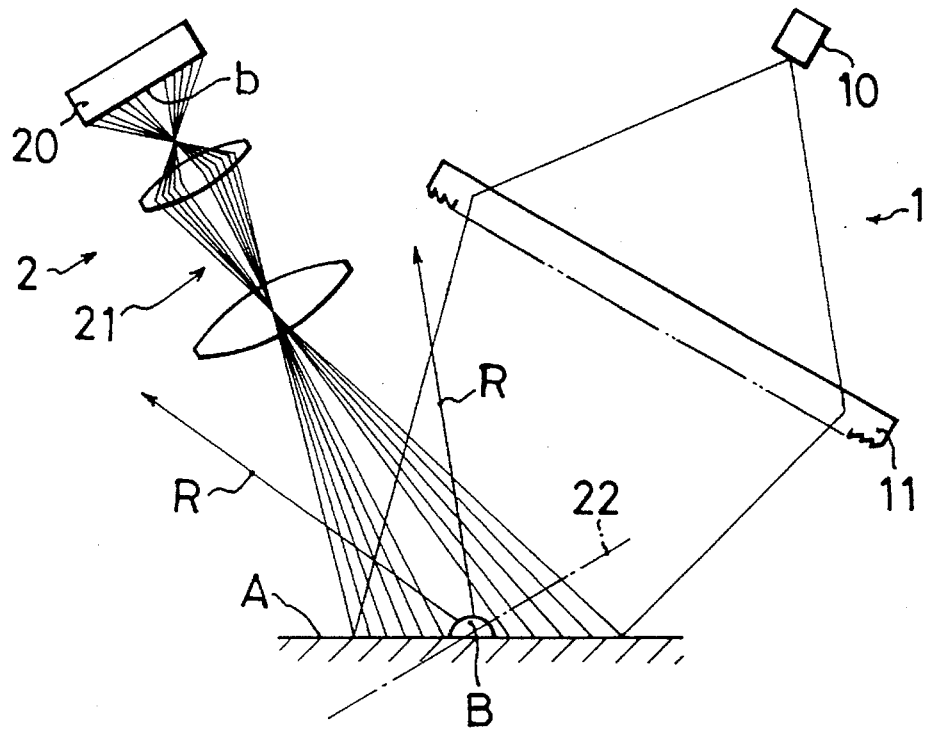
FIGS. 8A and 8B are diagrams showing the relationship between the picturing means and the workpiece in a conventional example.
Figure 8B:
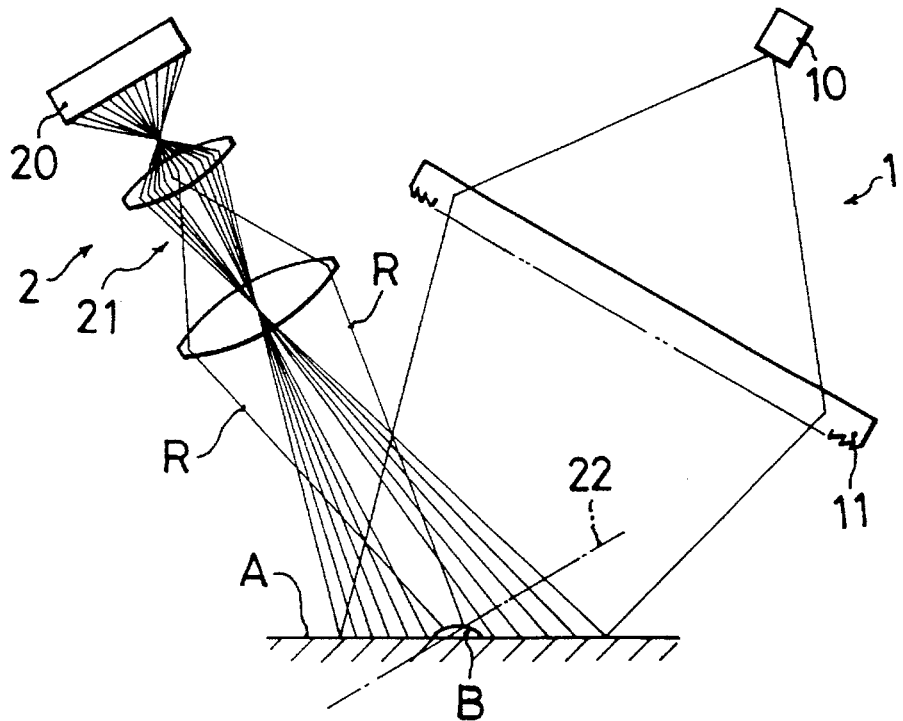

The optical inspection apparatus is made up, like the one shown in FIG. 8A, of a projecting means 1 and a picturing means 2 which comprises a CCD camera. The light from a light source 10 of the projecting means 1 is introduced to an optical converging system 11 via optical fibers 12 to radiate the light towards the workpiece surface A. The reflected light of the radiated detecting light as reflected from the workpiece surface A is received by the picturing means 2, and image data of the picturing means 2 are transmitted to an image processing apparatus 4. That dark portion within the image which appears due to a defective portion with a projection and a depression in the form of dust or the like on the workpiece surface A is thus arranged to be detected. To the image processing apparatus 4 there is inputted, from a robot controller 5, information relating to the position of inspection.

Figure 2:
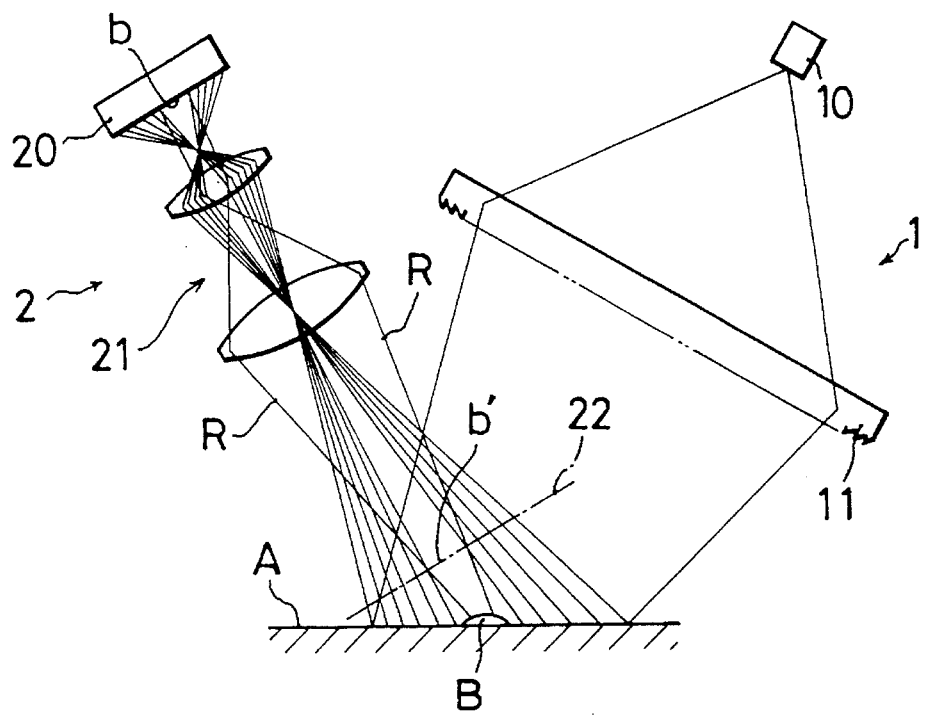
FIG. 2 is a diagram showing the relationship between a picturing means and a workpiece according to the present invention.

As shown in FIG. 2, in the above-described inspecting position, the focal surface 22 of the picturing means 2 is positioned away from the workpiece surface A to the side of the picturing means 2 relative to the entire region of the effective inspecting range of the workpiece surface A.

On the image surface 20 of the picturing means 2, there will be faithfully formed an image of the reflected light on the focal surface 22 through an optical image-forming system 21. Here, even if the reflected light R from the defective portion B on the workpiece surface A is received by the picturing means 2, the reflected light R from the defective portion B will no longer be incident onto that portion b' corresponding to the defective portion B which is on the focal surface 22 positioned away from the workpiece surface A to the side of the picturing means 2, as long as the detecting light is reflected in diffusion, even to a small degree, at the defective portion B. This portion b' on the focal surface 22 will then be that portion b on the image surface 20 which corresponds to the defective portion B. This portion b will therefore become a dark portion without image formation by the reflected light R from the defective portion B.

In this manner, the defective portion B which is present within the effective inspecting range is image-formed on the image surface 20 as a dark portion, however small it may be.

Figure 3:
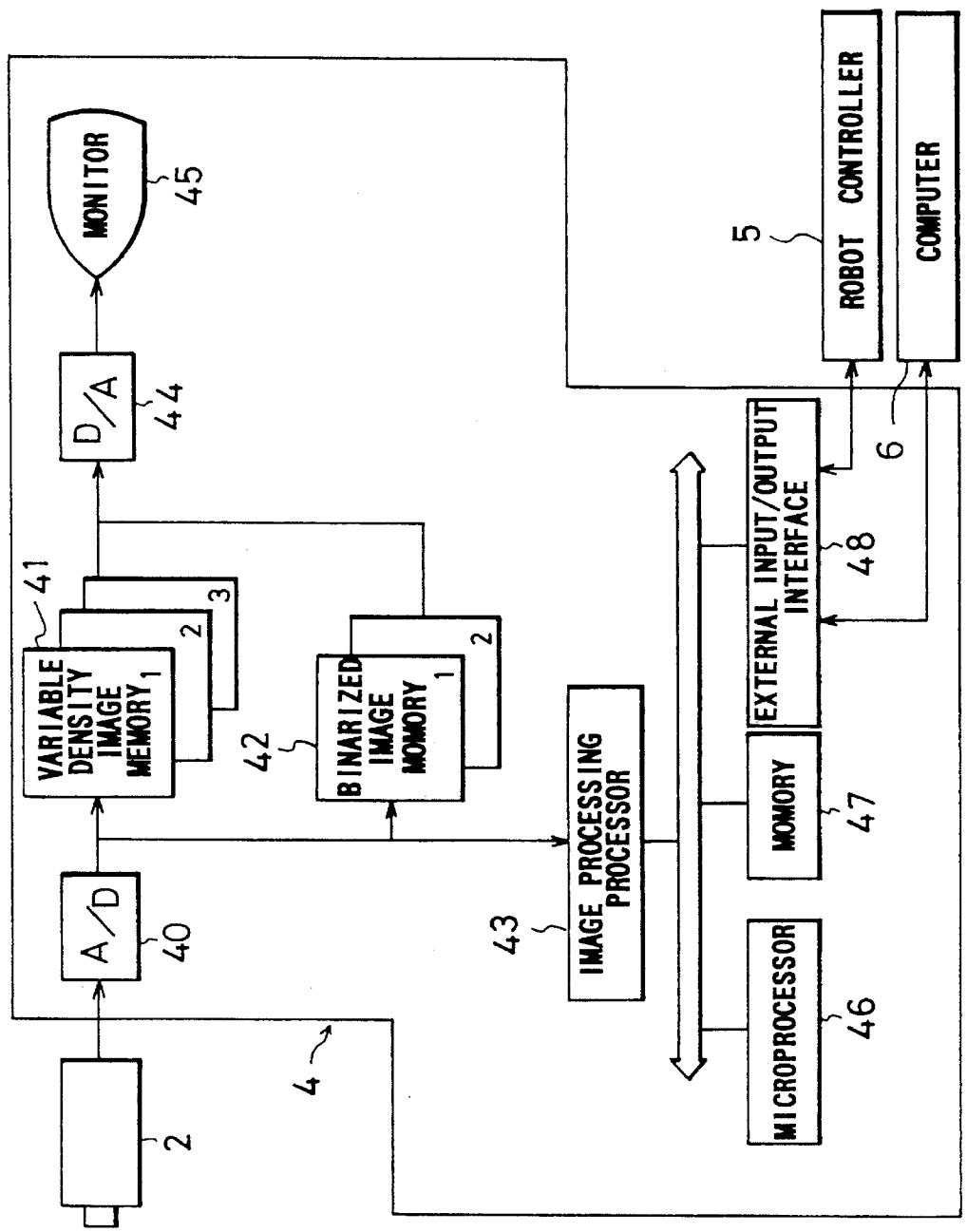
FIG. 3 is a block diagram showing an image processing apparatus of the inspection apparatus.
Figure 4:
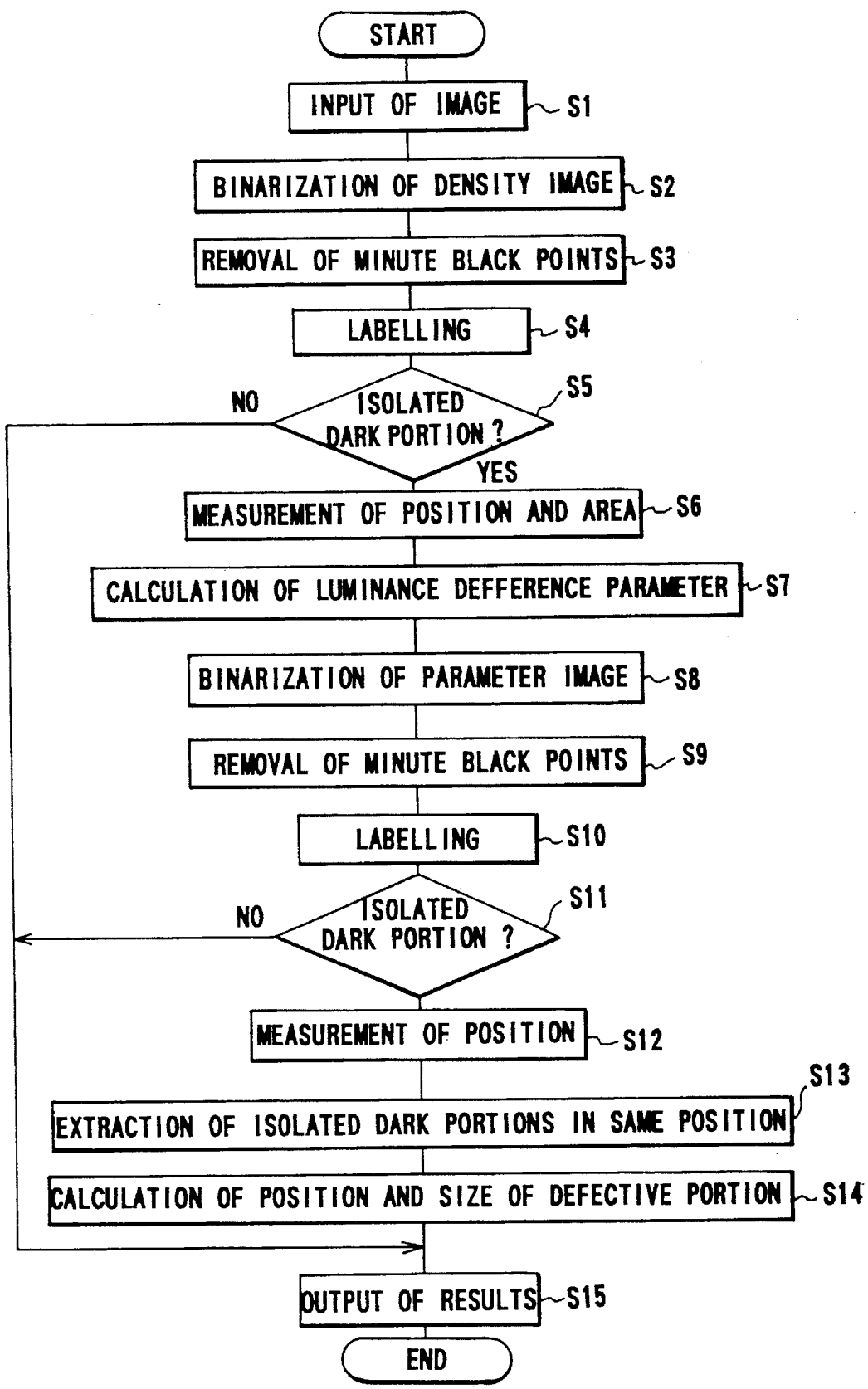
FIG. 4 is a flow chart showing one example of an image processing step.

The image processing apparatus 4 is provided, as shown in FIG. 3, with a variable density image memory 41 which stores variable density image data to be inputted from the picturing means 2 via an A/D converter 40, a binarized image memory 42, and an image processing processor 43. The variable density image data that are stored in the variable density image memory 41 are converted to binarized image data by the image processing processor 43 and are stored in the binarized image memory 42. Further, the image data that are stored in both the image memories 41, 42 are displayed, where necessary, on a monitor 45 via a D/A converter 44. To the image processing processor 43 there are connected a microprocessor 46, a memory 47 and an interface (I/F) 48. To the interface 48 there is connected the robot controller 5 and an external computer 6 for controlling the processed results.

Next, an explanation will now be made, with reference to FIG. 4 and FIGS. 5A through 5F, about the image processing procedure in the image processing apparatus 4.

Figure 5A:
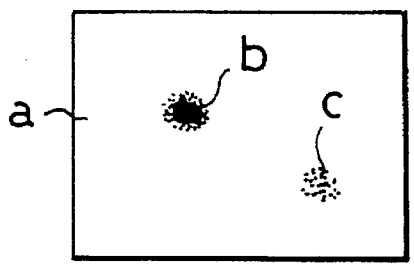
FIG. 5A is diagram showing the density image to be taken into from the picturing means.

First, the density image data from the picturing means 2 are inputted to No. 1 memory of the density image memory 41 (S1). FIG. 5A represents an image that is taken into by the picturing means 2. In this example, inside a bright portion "a" in which the reflected light from a smooth portion of the workpiece surface A is image-formed, there exist a dark portion b which is attributable to the defective portion having a projection and a depression on the workpiece surface A, and that dark portion c with a lower luminance than the normal bright portion "a" which is attributable to unevenness of luminance. The luminance distribution of each of these portions is as shown in FIG. 5B.

Figure 5B:
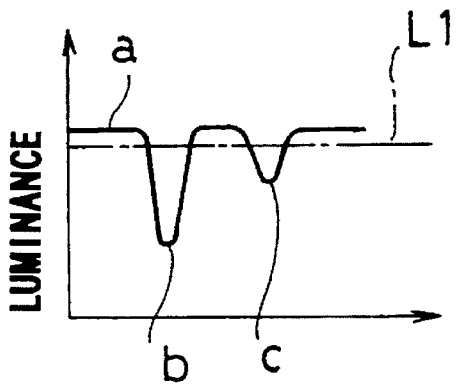
FIG. 5B is a diagram showing the luminance distribution of the density image.
Figure 5C:
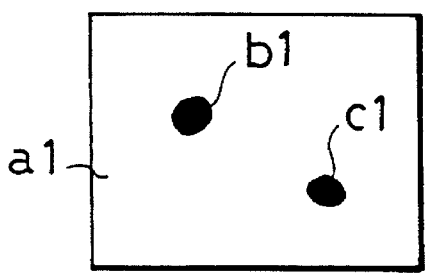
FIG. 5C is a diagram showing a binarized image based on the luminance.

Then, the density image is binarized on the basis of a threshold value which is a relatively high luminance as shown by L1 in FIG. 5B and which is set such that a portion of relatively high luminance on the periphery of the dark portion b is also binarized as a dark portion. The data of the first binarized image thus obtained are inputted into No. 1 memory of the binarized image memory 42 (S2). In this binarized image there appear, as shown in FIG. 5C, inside the bright portion a1 corresponding to the above-described bright portion "a", a dark portion b1 which is a substantial congruence of the above-described dark portion b, and a dark portion c1 which corresponds to the above-described dark portion c. Then, minute black points due to noises or the like are removed (S3) and thereafter those dark portions which are present as independent lumps are extracted and labelled (S4). Then, a determination is made as to whether each of the dark portions is an isolated one or not in the bright portion (S5). When there is an isolated dark portion, the area and the position thereof (dark portions b1 and c1 in this example) are measured and stored (S6).

Then, there is calculated a parameter value of each picture element of the density image based on the difference in luminance of the surrounding picture elements. The data of this parameter value are inputted into No. 2 memory of the density image memory 41 (S7). In this case, in order to emphasize the difference in luminance, it is preferable to calculate the parameter value as a powered value of the difference in luminance, e.g., a value to the second power. For example, the luminance of the picture element in the coordinates of (n, m) on the image is defined to be fnm, and the parameter value Fnm based on the difference in luminance of the picture elements in the surrounding coordinates (n−1 through n+1, m−1 through m+1) is calculated by the following formula $$Fnm = \sum_{i=n-1}^{n+1} \sum_{j=m-1}^{m+1} (fnm - fij)^2$$

Figure 5D:
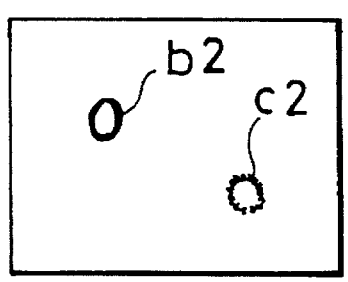
FIG. 5D is a diagram showing an image of a parameter value based on the luminance difference.

The image (negative image) of this parameter value is as shown in FIG. 5D, in which there appear ring-like dark portions b2, c2 in the portions corresponding to each of the dark portions b, c. Here, when the luminance distribution characteristics are compared between the dark portion b which is attributable to the defective portion and the dark portion c which is attributable to unevenness of luminance, the luminance change is steeper at the dark portion b as shown in FIG. 5B. The parameter value becomes far larger, as shown in FIG. 5E, at the ring-like dark portion b2 corresponding to the dark potion b than at the ring-like dark portion c2 corresponding to the dark portion c.

Figure 5E:
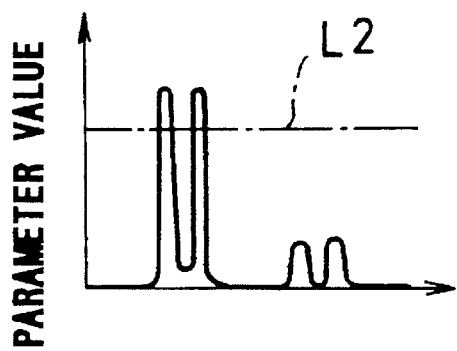
FIG. 5E is a diagram showing the distribution of the parameter value.
Figure 5F:
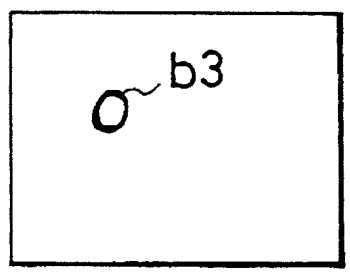
FIG. 5F is a diagram showing the binarized image based on the parameter value.

Then, the image of the parameter value is binarized on the basis of a binarizing threshold value which is shown as L2 in FIG. 5E and which is set so as to be higher than the parameter value of the dark portion which is attributable to the unevenness of the luminance. The second binarized image thus obtained is inputted into No. 2 memory of the binarized image memory 42 (S8). This binarized image (negative image) will be as shown in FIG. 5F, in which a ring-like dark portion b3 appears only in the portion which corresponds to the dark portion b attributable to the defective portion. Then, a processing of removing the minute black points and a processing of labelling are carried out on the second binarized image (S9, S10). When there is an isolated dark portion inside the bright portion, the positional data of this dark portion (dark portion b3 in this example) are measured and stored in memory (S11, S12).

Then, a comparison is made between the positional data of the isolated dark portions in the first binarized image and the positional data of the isolated dark portions in the second binarized image. Among the isolated dark portions of the first binarized image, those dark portions which are present in the same positions as the isolated dark portions of the second binarized image are extracted as the dark portions attributable to the defective portion (S13). Based on the positional data and the area data of these dark portions (the dark portion of b1 in this example), the position and the size of the defective portions are calculated (S14) and the results are outputted to the computer 6 (S15).

When there is no isolated dark portion in the first binarized image, the calculation of the parameter is not carried out and, instead, the program proceeds to S15 to output a result that there is no defective portion. When there is no isolated dark portion in the second binarized image, there is similarly outputted a result that there is no defective portion.

If the calculation of the above-described parameter values is made for all of the picture elements, the time for processing will become long. As a solution, each window may be set so as to enclose each portion which has become an isolated dark portion in the first binarized image so that a calculation may be made only for the picture elements within each window.

By the way, if the workpiece surface is curved, the reflected light will be diffused and, therefore, the effective inspection range from which the picturing means can receive the reflected light is narrowed. As a result, there will appear on the image irregular shade in a position on the boundary of the effective inspection range. If this image is simply binarized, there is a possibility that the shade portion appears on the binarized image as an independent dark portion. As a solution, in the conventional art, the shade portion is removed by carrying out a processing of enlarging and contracting the binarized image. The time for processing therefore becomes long. However, since the parameter value of the shade portion becomes small if the parameter value is calculated as described above, there is no possibility that the shade portion in the second binarized image becomes an isolated dark portion. Even if the shade portion may appear on the first binarized image as an independent dark portion, there is no possibility that this isolated dark portion is wrongly detected as the defective portion. Therefore, it is possible to omit the processing of enlarging and contracting the binarized image, thereby shortening the processing time.

In case the detecting accuracy with respect to the size of the defective portion is not so strictly required, it may be so arranged that the defective portion is detected only by the second binarized image, i.e., the binarized image of the above-described parameter value instead of obtaining the first binarized image.

Figure 6:
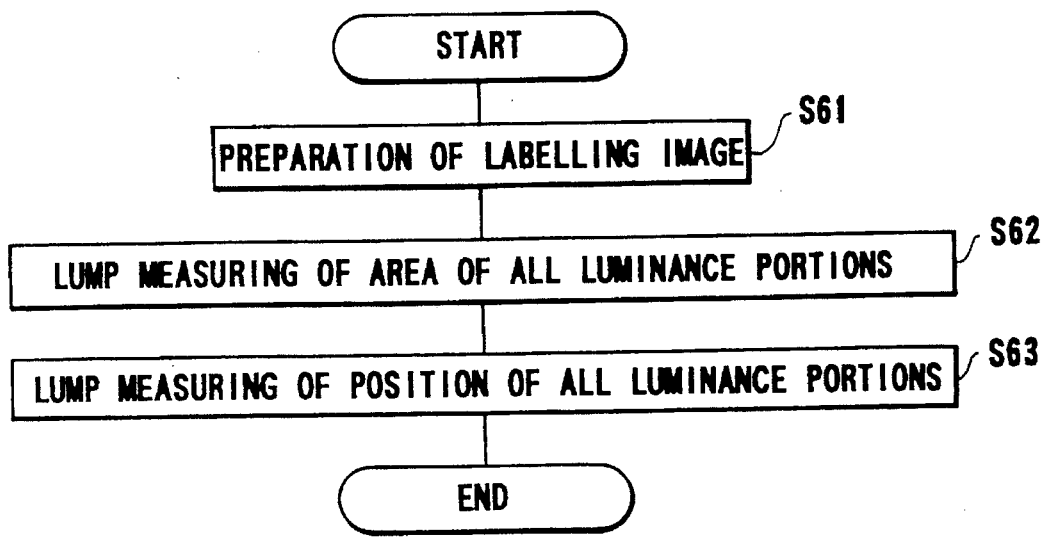
FIG. 6 is a flow chart showing the step of measuring the position and the area of a dark portion.

In measuring the position and the area of each dark portion in the above-described step S6, it is also possible to extract each dark portion, one by one, to thereby measure both the items of position and area. In this example, however, the processing of data measuring in step S6 is arranged to be carried out in the procedure as shown in FIG. 6.

Figure 7A:
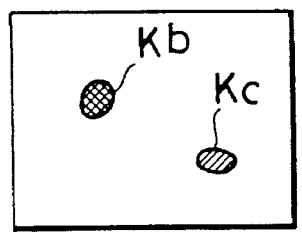
FIG. 7A is a diagram showing the labelling image.

Namely, there is first prepared a labelling image as shown in FIG. 7A in which each of the isolated dark portions appearing in the first binarized image is represented in different luminances (S61). This labeling image is inputted into No. 3 memory of density image memory 41. In this example, the dark portions b1 and c1 are represented on the labelling image in the respective luminances of Kb and Kc.

Figure 7B:
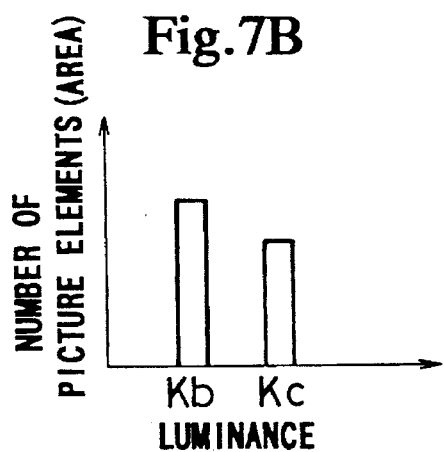
FIG. 7B is a histogram showing the area of each luminance portion of the labelling image.

Then, there is prepared a histogram, as shown in FIG. 7B, which represents the number of picture elements in each luminance portion in the labelling image. The area of all the luminance portions is measured in a lump and the area of each luminance portion is stored in memory (S62). Further, the labelling image is scanned in the directions of two coordinates of the image, i.e., the x-axis coordinate and the y-axis coordinate, over the entire area thereof. The positions of all luminance portions in the x-axis direction and the y-axis direction are respectively measured in a lump and the positions of each luminance is stored in memory (S63). The area and the position thus measured coincide with the area and the position of each dark portion which corresponds to each luminance portion. In this example, the area and the position of the luminance portion of Kb coincides with the area and the position of the dark portion of b1, and the area and the position of the luminance portion of Kc coincide with the area and the position of the dark portion of c1.

In case each dark portion within the image is independently extracted to measure the area and the position thereof, the processing time required to measure the data for each dark portion is about 20 msec. In case measurement is made in a lump, item by item, about each item such as the area and the position by scanning the entire range of the labelling image as in the present example, the processing time required for measuring data in each item will become as long as about 50 msec. However, since this processing time becomes constant regardless of the number of the dark portions, the total processing time required for data measuring of all items also becomes constant. Therefore, in inspecting by an on-line system, it is not necessary, unlike the conventional method, to set the processing time longer considering the processing time when the dark portions appear in a large number. This results in an improved efficiency in the inspection. In addition, in case each of the dark portions is extracted one by one to measure the data, it was necessary, in order to prevent the failure to extract the dark portions in the image, to carry out the processing of confirming the termination of extraction of all the dark portions before the robot 3 can be operated to move the optical inspecting apparatus to the next inspecting position. In this example, however, this kind of processing of confirming the termination becomes needless and is, in that sense also, more efficient.

It is readily apparent that the above-described method of inspecting a workpiece surface meets all of the objects mentioned above and also has the advantage of wide commercial utility. It should be understood that the specific form of the invention hereinabove described is intended to be representative only, as certain modifications within the scope of these teachings will be apparent to those skilled in the art.

Accordingly, reference should be made to the following claims in determining the full scope of the invention.

What is claimed is:

1. A method of inspecting a workpiece surface for detecting a defective portion on the workpiece surface by using an optical inspecting apparatus having a projector for radiating a detecting light towards the workpiece surface and a picturing means for receiving a reflected light from the workpiece surface, said method comprising the steps of:

picturing with the picturing means the reflected light in a condition in which a focal plane of the picturing means is positioned between the workpiece surface and the picturing means such that the focal plane does not intersect the workpiece surface anywhere in an inspecting region of the workpiece surface from which the picturing means can receive the reflected light; and processing an image to detect the defective portion on the workpiece surface in the inspecting region from a dark portion which appears on the image of the picturing means.

2. A method of inspecting a workpiece surface according to claim 1, wherein said step of processing the image further comprises the steps of:

obtaining a predetermined parameter value for each of picturing elements of the picturing means based on a difference in luminance between one picturing element and its surrounding picturing elements; and selecting a dark portion which is positioned in a portion in which the parameter value becomes large, as a dark portion which is attributable to the defective portion on the workpiece surface.

3. A method of inspecting a workpiece surface according to claim 2, wherein said step of processing the image further comprises the steps of:

preparing a binarized image by binarizing the image in the picturing means based on a relatively high luminance threshold value which is set such that a portion around a dark portion which appears on the image and which has a relatively high luminance is also binarized as a dark portion; and locating a position and a size of the defective portion on the workpiece surface based on the position and the area of the dark portion that has been selected based on the parameter value among the dark portions appearing on the binarized image.

4. A method of inspecting a workpiece surface according to claim 2 or 3, wherein said parameter value is a powered value of the difference in luminance.

5. A method of inspecting workpiece surface according to claim 1, wherein said step of processing the image further comprises the step of measuring data of a plurality of items such as the position and the area of each dark portion which appears on the image of the picturing means and wherein said step of measuring data of the plurality of items further comprises the steps of:

preparing a labelling image which indicates each of the dark portions by different luminances; and measuring, in a lump, the data of the plurality of items based on the labelling image, one by one, relative to all of the dark portions.

* * * * *